(12) United States Patent
Yun et al.

(10) Patent No.: US 9,115,331 B2
(45) Date of Patent: Aug. 25, 2015

(54) 3,3-DIETHYL-ALKYL-2-OXA-SPIRO[4.5]DEC-7-ENES AND THEIR USE IN PERFUME COMPOSITIONS

(71) Applicants: Heedong Yun, Tenafly, NJ (US); Ryan D. Oesterle, Jackson, NJ (US); Adam P. Closson, Jersey City, NJ (US)

(72) Inventors: Heedong Yun, Tenafly, NJ (US); Ryan D. Oesterle, Jackson, NJ (US); Adam P. Closson, Jersey City, NJ (US)

(73) Assignee: International Flavors & Fragrances Inc. NY (US)

( * ) Notice: Subject to any disclaimer, the term of this patent is extended or adjusted under 35 U.S.C. 154(b) by 61 days.

(21) Appl. No.: 13/888,742

(22) Filed: May 7, 2013

(65) Prior Publication Data
US 2014/0336103 A1    Nov. 13, 2014

(51) Int. Cl.
*C11B 9/00* (2006.01)
*C07D 307/94* (2006.01)

(52) U.S. Cl.
CPC ............ *C11B 9/0076* (2013.01); *C07D 307/94* (2013.01)

(58) Field of Classification Search
CPC ....................................................... C11B 9/0076
USPC .............................. 512/13; 549/429, 331, 356
See application file for complete search history.

(56) References Cited

U.S. PATENT DOCUMENTS 5,510,326 A * 4/1996 Noire ............................. 512/11

* cited by examiner

*Primary Examiner* — Ling Choi
*Assistant Examiner* — Lanee Reuther
(74) *Attorney, Agent, or Firm* — XuFan Tseng; Martin Zhang; Elizabeth M. Quirk

(57) ABSTRACT

The present invention is directed to novel 3,3-diethyl-alkyl-2-oxa-spiro[4.5]dec-7-ene compounds and a method of improving, enhancing or modifying a fragrance formulation through the addition of an olfactory acceptable amount of these novel compounds.

16 Claims, No Drawings

3,3-DIETHYL-ALKYL-2-OXA-SPIRO[4.5]DEC-7-ENES AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

SUMMARY OF THE INVENTION

The present invention provides novel chemicals and their unexpected advantageous use in enhancing, improving or modifying the fragrance of perfumes, colognes, toilet waters, fabric care products, personal products and the like.

More specifically, the present invention is directed to novel 3,3-diethyl-alkyl-2-oxa-spiro[4.5]dec-7-ene compounds that exhibit unexpected fragrance effect, particularly fruity, green, and woody notes, and a method of improving, enhancing or modifying a fragrance formulation through the addition of an olfactory acceptable amount of 3,3-diethyl-alkyl-2-oxa-spiro[4.5]dec-7-enes represented by Formula I set forth below:

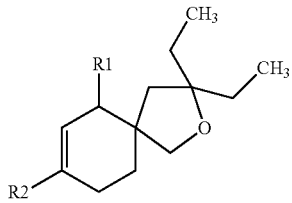

Formula I wherein $R^1$ and $R^2$ are independently selected from the group consisting of hydrogen and methyl.

These and other embodiments of the present invention will be apparent by reading the following specification.

DETAILED DESCRIPTION OF THE INVENTION

It is known to those with the skill in the art that Formula I as defined above provides the following novel compounds:

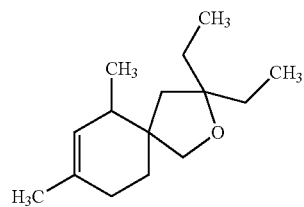

Formula II

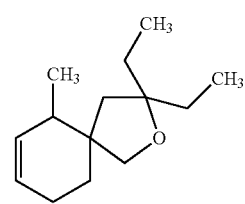

Formula III

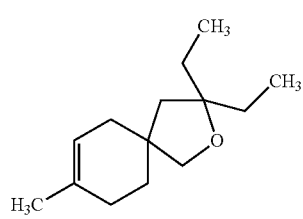

Formula IV

Formula V

Those with the skill in the art will recognize that:

Formula II represents 3,3-diethyl-6,8-dimethyl-2-oxa-spiro[4.5]dec-7-ene;

Formula III represents 3,3-diethyl-6-methyl-2-oxa-spiro[4.5]dec-7-ene;

Formula IV represents 3,3-diethyl-8-methyl-2-oxa-spiro[4.5]dec-7-ene; and

Formula V represents 3,3-diethyl-2-oxa-spiro[4.5]dec-7-ene.

The compounds of the present invention can be prepared from 3-methylene-dihydro-furan-2,5-dione (commercially available). The reaction steps can be depicted by the scheme shown as follows:

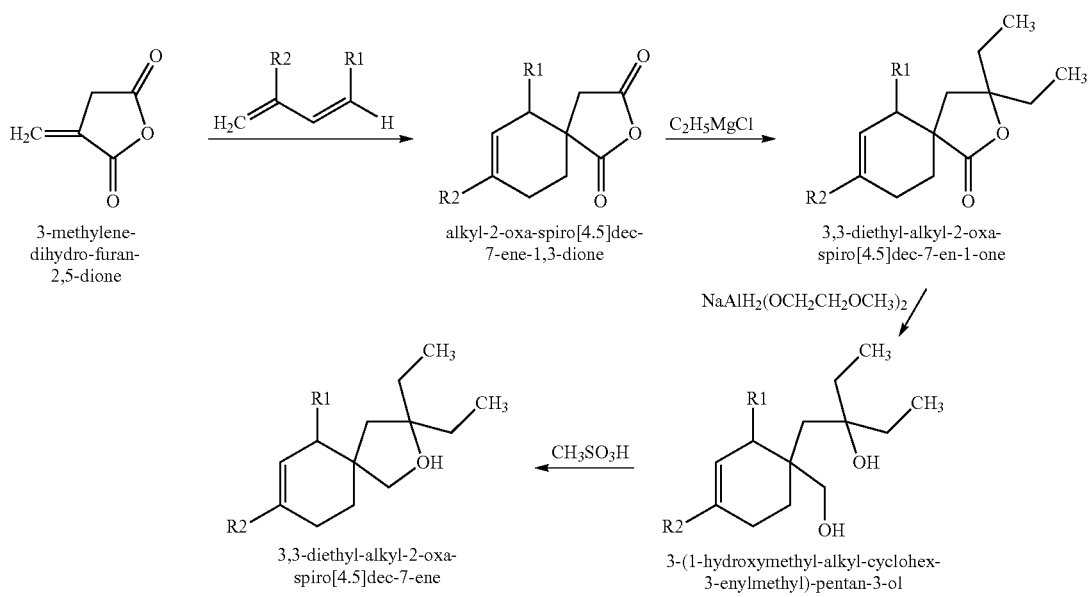

wherein $R^1$ and $R^2$ are defined as above.

Those with skill in the art will recognize that the alkyl-2-oxa-spiro[4.5]dec-7-ene contained in the compounds of the present invention gives rise to a number of positional and trans- and cis-isomers. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning products, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk; and flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), 2-ethyl-4-(2,2,3-trimethyl-3-cyclopenten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6- trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methylpentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention may comprise a compound of the present invention and further a complementary fragrance compound as defined above.

The term "fragrance product" means a consumer product that adds a fragrance or masks a malodor. Fragrance products may include, for example, perfumes, colognes, toilet water, personal care products such as soaps, shower gels, and hair care products, fabric care products, air fresheners, cosmetic products, and cleaning products such as detergents, dishwashing compositions, scrubbing compounds, and window cleaners. The fragrance product of the present invention is a consumer product that contains a compound of the present invention. The fragrance product of the present invention may contain a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 50 weight percent, preferably from 0.1 to about 25 weight percent, and more preferably from about 0.5 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides fruity, green, and woody notes that make the fragrance formulation more desirable and noticeable and add the perception of value. All of the odor qualities found in this material assist in beautifying and enhancing the finished accord improving the performance of the other materials in the fragrance. The fruity side is found in many fragrances today which happens to be very trendy, especially for the younger consumers.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, M is understood to be molar, L is understood to be liter, mL is understood to be milliliter, and g is understood to be gram. IFF as used in the examples is understood to mean International Flavors & Fragrances Inc., New York, N.Y., USA.

Example I

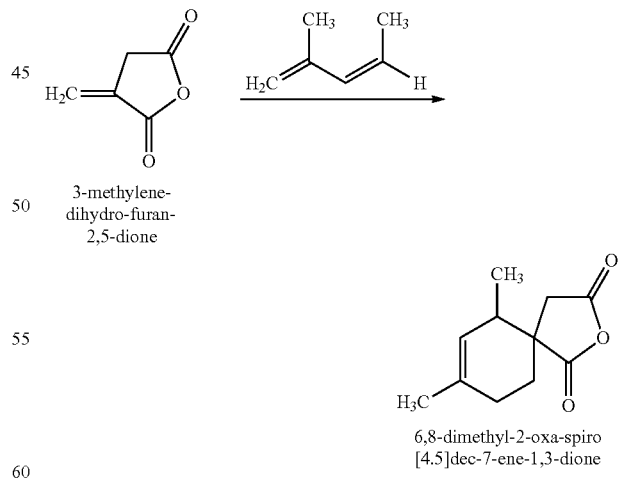

3-methylene-dihydro-furan-2,5-dione 6,8-dimethyl-2-oxa-spiro[4.5]dec-7-ene-1,3-dione Preparation of
6,8-Dimethyl-2-oxa-spiro[4.5]dec-7-ene-1,3-dione 3-Methylene-dihydro-furan-2,5-dione (400 g) and 2-methyl-penta-1,3-diene (352 g) were charged into an autoclave and heated to about 65° C. The reaction was exothermic and temperature increased rapidly. When temperature reached about 250° C., the reaction was cooled to room temperature. The resulting mixture was then recrystallized with isopropanol (CH$_3$CH(CH$_3$)OH) to afford 6,8-dimethyl-2-oxa-spiro [4.5]dec-7-ene-1,3-dione (692 g).

$^1$H NMR (CDCl$_3$, 400 MHz): 5.26 ppm (m, ~63% of 1H), 5.12 ppm (~37% of 1H), 2.80 ppm (s, 2H), 1.63-2.79 ppm (m, 5H), 1.70 ppm (s, 3H), 1.07 ppm (d, ~63% of 3H, J=6.85 Hz), 0.95 ppm (d, ~37% of 3H, J=7.15 Hz)

Example II

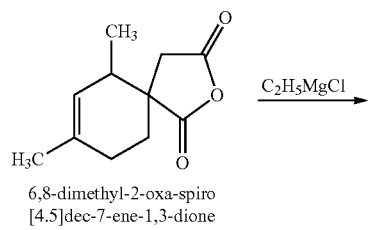

6,8-dimethyl-2-oxa-spiro
[4.5]dec-7-ene-1,3-dione

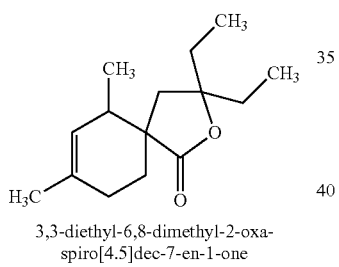

3,3-diethyl-6,8-dimethyl-2-oxa-
spiro[4.5]dec-7-en-1-one

Preparation of 3,3-Diethyl-6,8-dimethyl-2-oxa-spiro [4.5]dec-7-en-1-one 6,8-Dimethyl-2-oxa-spiro[4.5]dec-7-ene-1,3-dione (prepared as above in EXAMPLE I, 140 g) was fed slowly into an ethyl magnesium chloride (C$_2$H$_5$MgCl) solution in tetrahydrofuran (THF) (2 M, 1.53 L) while the temperature was kept under 25° C. After the feeding was completed, the reaction was aged at room temperature for about an hour. The reaction mixture was then poured into hydrochloric acid (HCl) (2 M) containing ice. Toluene was added. The organic and aqueous layers were shaken in a separatory funnel and separated. The aqueous layer was further washed with toluene. The organic layers were combined and washed with sodium carbonate (Na$_2$CO$_3$) solution until basic. The resulting solution was distilled to afford 3,3-diethyl-6,8-dimethyl-2-oxa-spiro[4.5] dec-7-en-1-one (170 g).

$^1$H NMR (CDCl$_3$, 400 MHz): 5.26 ppm (m, ~67% of 1H), 5.09 ppm (~33% of 1H), 2.65 ppm (m, ~33% of 1H), 2.24 ppm (~67% of 1H), 1.52-2.13 ppm (m, 7H), 1.93 ppm (d, 2H, J=10.71 Hz), 1.68 ppm (s, ~67% of 3H), 1.65 ppm (s, ~33% of 3H), 1.07 ppm (d, ~67% of 3H, J=7.05 Hz), 0.89-0.96 ppm (m, 7H)

Example III

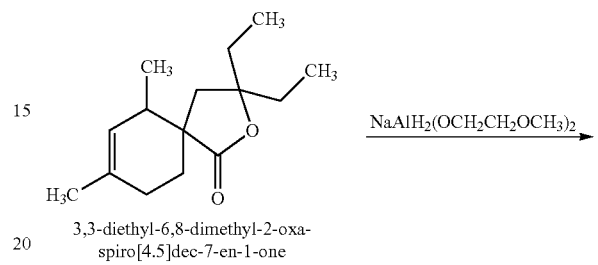

3,3-diethyl-6,8-dimethyl-2-oxa-
spiro[4.5]dec-7-en-1-one

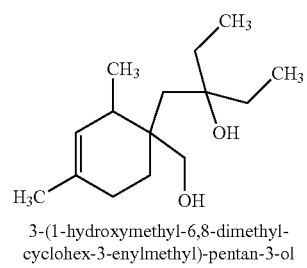

3-(1-hydroxymethyl-6,8-dimethyl-
cyclohex-3-enylmethyl)-pentan-3-ol

Preparation of 3-(1-Hydroxymethyl-6,8-dimethyl-cyclohex-3-enylmethyl)-pentan-3-ol A round-bottom reaction flask was charged with Vitride® reducing agent (a solution of sodium bis(2-methoxyethoxy) aluminum dihydride (NaAlH$_2$(OCH$_2$CH$_2$OCH$_3$)$_2$) in toluene) (65%, 420 g) under a nitrogen atmosphere and heated to 85° C. 3,3-Diethyl-6,8-dimethyl-2-oxa-spiro[4.5]dec-7-en-1-one (prepared as above in EXAMPLE II) (295 g) was fed in dropwise under nitrogen while the temperature was maintained at about 85° C. After 3,3-diethyl-6,8-dimethyl-2-oxa-spiro[4.5]dec-7-en-1-one was consumed, the reaction mixture was aged at 85° C. for an hour, cooled to room temperature and quenched with isopropanol (100 mL). Sodium hydroxide (50%, 500 mL) was then added. The resulting mixture was heated to 50° C. with stirring, aged at 50° C. for an hour and cooled to room temperature. The organic and aqueous layers were shaken in a separatory funnel and separated in a separatory funnel. The organic layer was then distilled to remove toluene solvent and to azeotropically dry the solution to afford crude product 3-(1-hydroxymethyl-6,8-dimethyl-cyclohex-3-enylmethyl)-pentan-3-ol (295 g).

Example IV

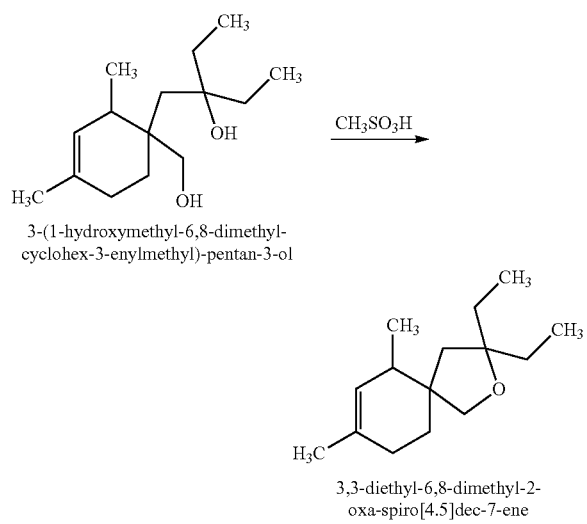

3-(1-hydroxymethyl-6,8-dimethyl-cyclohex-3-enylmethyl)-pentan-3-ol 3,3-diethyl-6,8-dimethyl-2-oxa-spiro[4.5]dec-7-ene Preparation of
3,3-Diethyl-6,8-dimethyl-2-oxa-spiro[4.5]dec-7-ene
(Formula II)

Crude 3-(1-hydroxymethyl-6,8-dimethyl-cyclohex-3-enylmethyl)-pentan-3-ol (prepared as above in EXAMPLE III) (295 g), toluene (500 mL) and methanesulfonic acid ($CH_3SO_3H$) (3 g) were charged into a 5 L round-bottom reaction flask fitted with a Bidwell-Sterling trap at room temperature. The reaction mixture was then heated to reflux and water was collected and removed via the Bidwell-Sterling trap. The reaction mixture was cooled to room temperature and transferred to a separatory funnel. The organic and aqueous layers were separated. The organic layer was washed with $Na_2CO_3$ solution until basic. The organic layer was further distilled to afford 3,3-diethyl-6,8-dimethyl-2-oxa-spiro[4.5]dec-7-ene (237 g).

$^1$H NMR (500 MHz, $CDCl_3$): 5.24-5.28 ppm (m, 1H), 3.67 ppm (d, ~64% of 1H, J=9.10 Hz), 3.60 ppm (d, ~36% of 1H, J=8.85 Hz), 3.52 ppm (d, ~36% of 1H, J=8.85 Hz), 3.43 ppm (d, ~64% of 1H, J=9.10 Hz), 1.88-2.09 ppm (m, 3H), 1.33-1.76 ppm (m, 11H), 0.96 ppm (d, ~36% of 3H, J=7.00 Hz), 0.90 ppm (d, ~64% of 3H, J=7.10 Hz), 0.85 ppm (t, 3H, J=7.48 Hz), 0.84 ppm (t, 3H, J=7.13 Hz).

The compound 3,3-diethyl-6,8-dimethyl-2-oxa-spiro[4.5]dec-7-ene was described as having woody, spicy, green and herbal notes.

Example V 3,3-Diethyl-6-methyl-2-oxa-spiro[4.5]dec-7-ene (Formula III) was prepared similarly according to EXAMPLE I-IV from 3-methylene-dihydro-furan-2,5-dione and penta-1,3-diene ($CH_2$=CHCH=CHCH_3$).

$^1$H NMR (500 MHz, $CDCl_3$): 5.58 ppm (m, 2H), 3.70 ppm (d, 1H, J=9.14 Hz), 3.44 ppm (d, 1H, J=9.14 Hz), 2.00-2.10 ppm (m, 3H), 1.35-1.72 ppm (m, 8H), 0.94 ppm (d, 3H, J=6.94 Hz), 0.85 ppm (t, 6H, J=7.57 Hz)

The compound 3,3-diethyl-6-methyl-2-oxa-spiro[4.5]dec-7-ene was described as having fruity, floral, fresh, green, minty, woody and spicy notes.

Example VI 3,3-Diethyl-8-methyl-2-oxa-spiro[4.5]dec-7-ene (Formula IV) was prepared similarly according to EXAMPLE I-IV from 3-methylene-dihydro-furan-2,5-dione and 2-methyl-buta-1,3-diene ($CH_2$=C(CH_3)CH=CH_2$).

$^1$H NMR (400 MHz, $CDCl_3$): 5.32 ppm (s, 1H), 3.54-3.56 ppm (m, 2H), 1.95-2.08 ppm (m, 4H), 1.63 ppm (s, 3H), 1.43-1.62 ppm (m, 8H), 0.82-0.87 ppm (m, 6H).

The compound 3,3-diethyl-8-methyl-2-oxa-spiro[4.5]dec-7-ene was described as having green, rhubarb, stemmy, woody and aldehydic notes.

Example VII

The fragrance properties of the above compounds (i.e., Formulas II-IV) were evaluated using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Chemical Name | Compound | Odor Profile | Strength | Complexity |
|---|---|---|---|---|
| 3,3-Diethyl-6,8-dimethyl-2-oxa-spiro[4.5]dec-7-ene (Formula II) | | woody, spicy, green and herbal | 4 | 4 |
| 3,3-Diethyl-6-methyl-2-oxa-spiro[4.5]dec-7-ene (Formula III) | | fruity, floral, fresh, green, minty, woody and spicy | 5.5 | 4 |

-continued

| Chemical Name | Compound | Odor Profile | Strength | Complexity |
| --- | --- | --- | --- | --- |
| 3,3-Diethyl-8-methyl-2-oxa-spiro[4.5]dec-7-ene (Formula IV) | 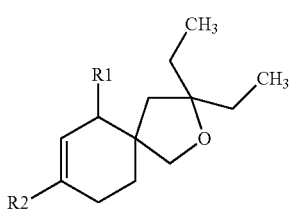 | green, rhubarb, stemmy, woody and aldehydic | 6 | 6 |

What is claimed is:

1. A compound of formula:

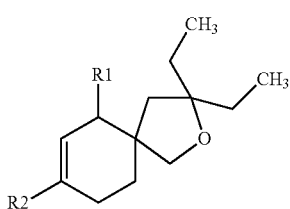

wherein $R^1$ and $R^2$ are independently selected from the group consisting of hydrogen and methyl.

2. The compound of claim 1, wherein the compound is selected from the group consisting of 3,3-diethyl-6,8-dimethyl-2-oxa-spiro[4.5]dec-7-ene, 3,3-diethyl-6-methyl-2-oxa-spiro[4.5]dec-7-ene and 3,3-diethyl-8-methyl-2-oxa-spiro[4.5]dec-7-ene.

3. A fragrance product containing an olfactory acceptable amount of the compound of claim 1.

4. The fragrance product of claim 3, wherein the compound of claim 1 is selected from the group consisting of 3,3-diethyl-6,8-dimethyl-2-oxa-spiro[4.5]dec-7-ene, 3,3-diethyl-6-methyl-2-oxa-spiro[4.5]dec-7-ene and 3,3-diethyl-8-methyl-2-oxa-spiro[4.5]dec-7-ene.

5. The fragrance product of claim 3, wherein the fragrance product is selected from the group consisting of a perfume, a cologne, toilet water, a cosmetic product, a personal care product, a fabric care product, a cleaning product and an air freshener.

6. The fragrance product of claim 5, wherein the cleaning product is selected from the group consisting of a detergent, a dishwashing composition, a scrubbing compound and a window cleaner.

7. A fragrance formulation containing an olfactory acceptable amount of a compound of formula:

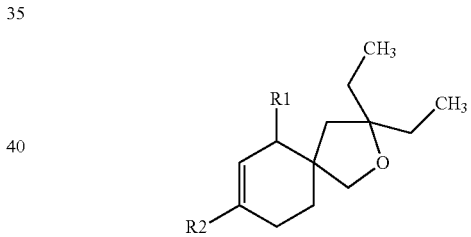

wherein $R^1$ and $R^2$ are independently selected from the group consisting of hydrogen and methyl.

8. The fragrance formulation of claim 7, wherein the compound is selected from the group consisting of 3,3-diethyl-6,8-dimethyl-2-oxa-spiro[4.5]dec-7-ene, 3,3-diethyl-6-methyl-2-oxa-spiro[4.5]dec-7-ene and 3,3-diethyl-8-methyl-2-oxa-spiro[4.5]dec-7-ene.

9. The fragrance formulation of claim 7, wherein the olfactory acceptable amount is from about 0.005 to about 50 weight percent of the fragrance formulation.

10. The fragrance formulation of claim 7, wherein the olfactory acceptable amount is from about 0.5 to about 25 weight percent of the fragrance formulation.

11. The fragrance formulation of claim 7, wherein the olfactory acceptable amount is from about 1 to about 10 weight percent of the fragrance formulation.

12. A method of improving, enhancing or modifying a fragrance formulation through the addition of an olfactory acceptable amount of a compound of formula:

wherein $R^1$ and $R^2$ are independently selected from the group consisting of hydrogen and methyl.

13. The method of claim 12, wherein the compound is selected from the group consisting of 3,3-diethyl-6,8-dimethyl-2-oxa-spiro[4.5]dec-7-ene, 3,3-diethyl-6-methyl-2-oxa-spiro[4.5]dec-7-ene and 3,3-diethyl-8-methyl-2-oxa-spiro[4.5]dec-7-ene.

14. The method of claim 12, wherein the olfactory acceptable amount is from about 0.005 to about 50 weight percent of the fragrance formulation.

15. The method of claim 12, wherein the olfactory acceptable amount is from about 0.5 to about 25 weight percent of the fragrance formulation.

16. The method of claim 12, wherein the olfactory acceptable amount is from about 1 to about 10 weight percent of the fragrance formulation.

* * * * *